(12) United States Patent
Yamada

(10) Patent No.: US 10,539,777 B2
(45) Date of Patent: Jan. 21, 2020

(54) OPTICAL UNIT AND ENDOSCOPE

(71) Applicant: FUJIFILM Corporation, Tokyo (JP)

(72) Inventor: Hideyuki Yamada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 207 days.

(21) Appl. No.: 15/706,769

(22) Filed: Sep. 18, 2017

(65) Prior Publication Data

US 2018/0039062 A1    Feb. 8, 2018

Related U.S. Application Data

(63) Continuation of application No. PCT/JP2016/058007, filed on Mar. 14, 2016.

(30) Foreign Application Priority Data

Mar. 31, 2015  (JP) ................. 2015-071818

(51) Int. Cl.
*G02B 23/24* (2006.01)
*A61B 1/04* (2006.01)
(Continued)

(52) U.S. Cl.
CPC ...... *G02B 23/2423* (2013.01); *A61B 1/00163* (2013.01); *A61B 1/04* (2013.01); *G02B 23/2476* (2013.01); *G02B 1/11* (2013.01)

(58) Field of Classification Search
CPC .......... G02B 23/2423; G02B 23/24; G02B 23/2476; G02B 1/11; A61B 1/00096; A61B 1/00163; A61B 1/04
(Continued)

(56) References Cited

U.S. PATENT DOCUMENTS 6,246,823 B1    6/2001    Kraas et al.
6,547,721 B1    4/2003    Higuma et al.
(Continued)

FOREIGN PATENT DOCUMENTS

GB    2321132    7/1998
JP    2000051143    2/2000
(Continued)

OTHER PUBLICATIONS

"International Search Report (Form PCT/ISA/210) of PCT/JP2016/058007", dated May 31, 2016, with English translation thereof, pp. 1-5.
(Continued)

*Primary Examiner* — Jennifer D. Carruth
(74) *Attorney, Agent, or Firm* — JCIPRNET

(57) ABSTRACT

Provided are an optical unit and an endoscope that can enhance the airtightness between a holding tube and a cover glass without a joining member flowing into a distal end surface of an optical lens while maintaining the attachment accuracy of the cover glass. A spacer is disposed between a cover glass position restricting part of a holding tube of an optical unit and a cover glass. The position of the cover glass in an optical axis is restricted by the cover glass position restricting part via a spacer. An external diameter of a first end surface of the spacer is smaller than an internal diameter of a cover glass fixing part of the holding tube. A solder pool part is provided in a region, which is surrounded by a side surface of the spacer, the cover glass fixing part, and the cover glass position restricting part.

8 Claims, 15 Drawing Sheets

(51) Int. Cl.
*A61B 1/00* (2006.01)
*G02B 1/11* (2015.01)

(58) Field of Classification Search
USPC .......................................... 359/513; 385/117
See application file for complete search history.

(56) References Cited

U.S. PATENT DOCUMENTS

| | | |
|---|---|---|
| 2002/0128535 A1 | 9/2002 | Kikuchi et al. |
| 2007/0118019 A1 | 5/2007 | Mitani et al. |
| 2012/0123210 A1* | 5/2012 | Eisenkolb ............ A61B 1/0011 600/160 |
| 2015/0065796 A1 | 3/2015 | Iwane |

FOREIGN PATENT DOCUMENTS

| | | |
|---|---|---|
| JP | 2000070214 | 3/2000 |
| JP | 2000139821 | 5/2000 |
| JP | 2000217775 | 8/2000 |
| JP | 2001128932 | 5/2001 |
| JP | 2002095626 | 4/2002 |
| JP | 2002336190 | 11/2002 |
| JP | 2006015076 | 1/2006 |
| JP | 2015047356 | 3/2015 |
| WO | 2013128681 | 9/2013 |

OTHER PUBLICATIONS

"International Preliminary Report on Patentability (Form PCT/IPEA/409) of PCT/JP2016/058007", dated on Jun. 13, 2017, with English translation thereof, pp. 1-16.

"Search Report of European Counterpart Application" dated May 17, 2018, p. 1-p. 5.

* cited by examiner

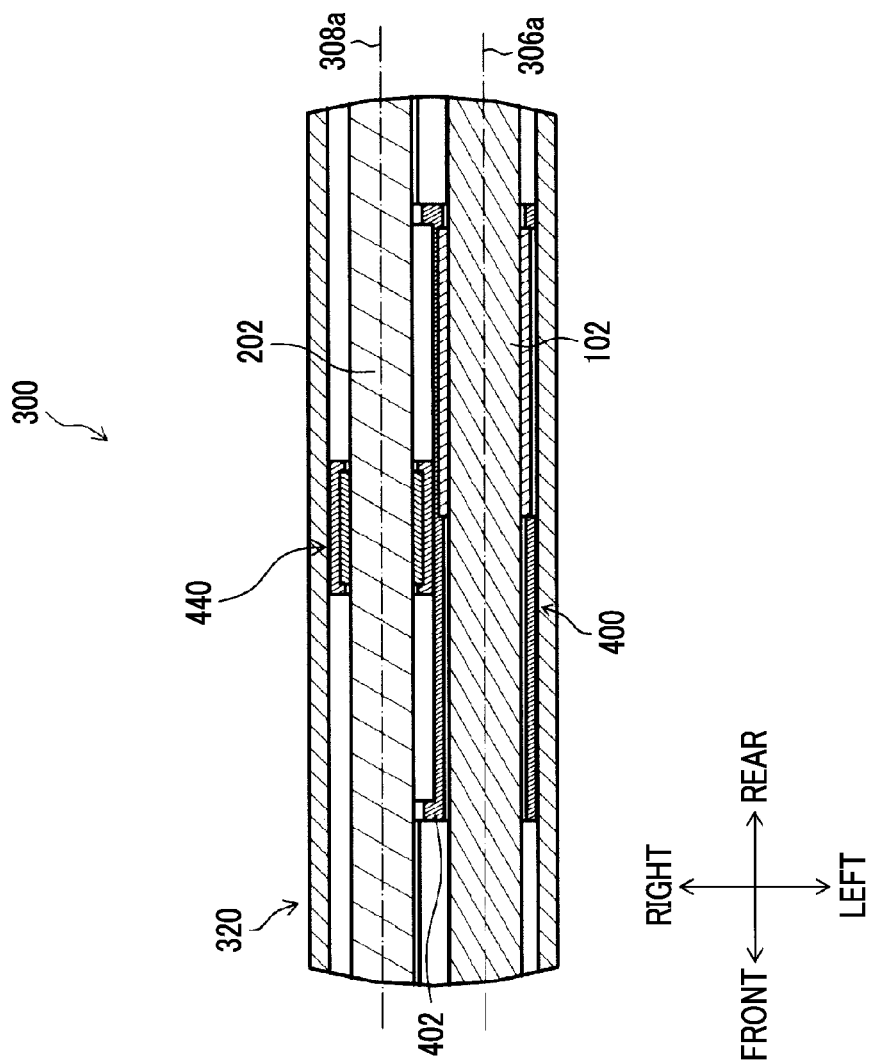

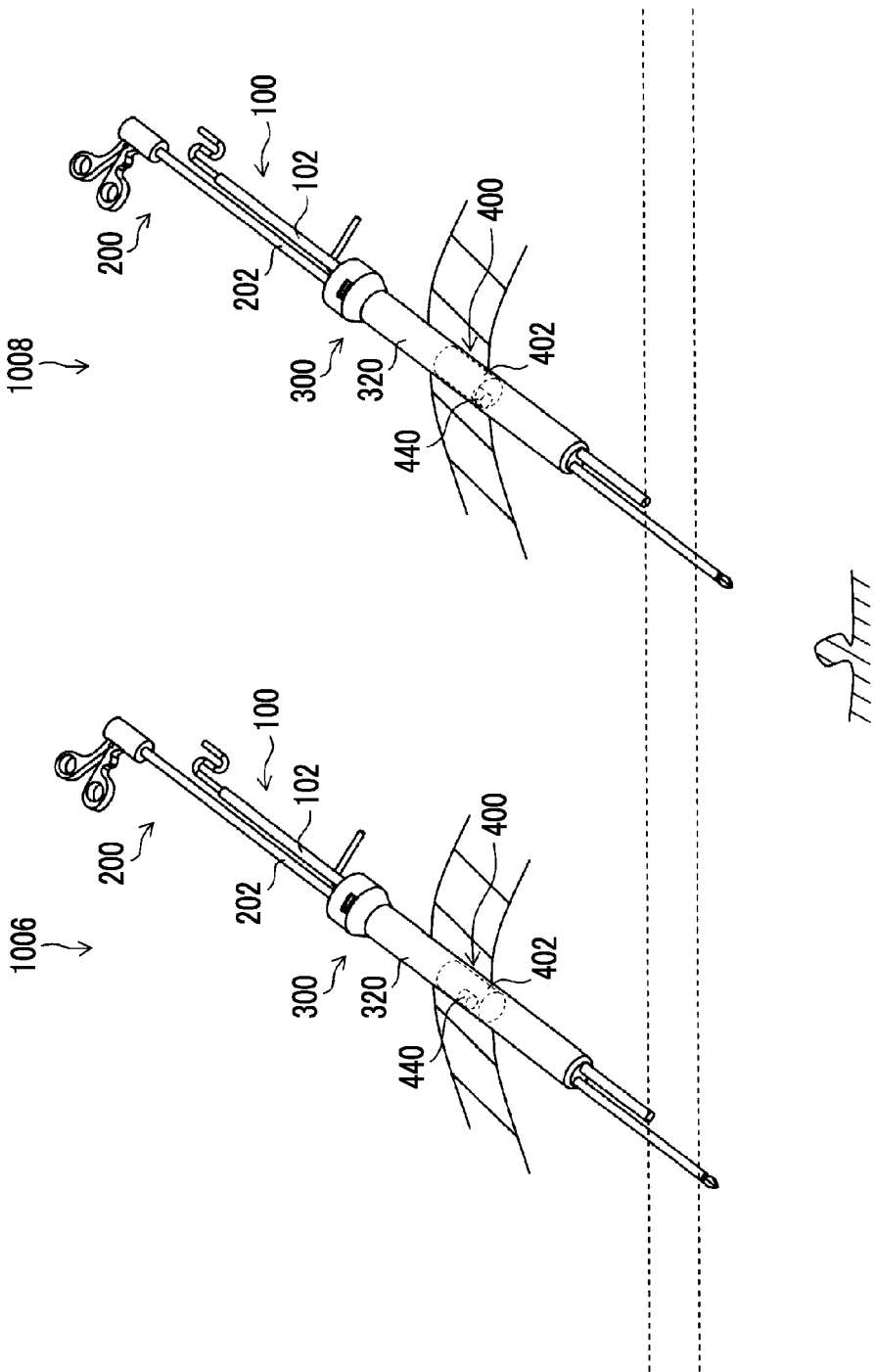

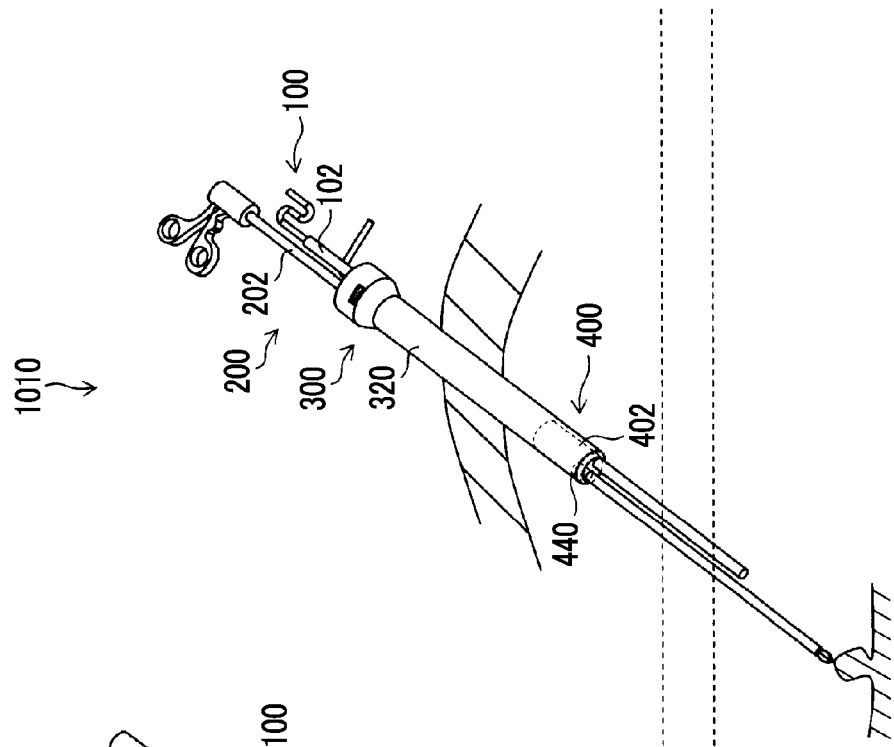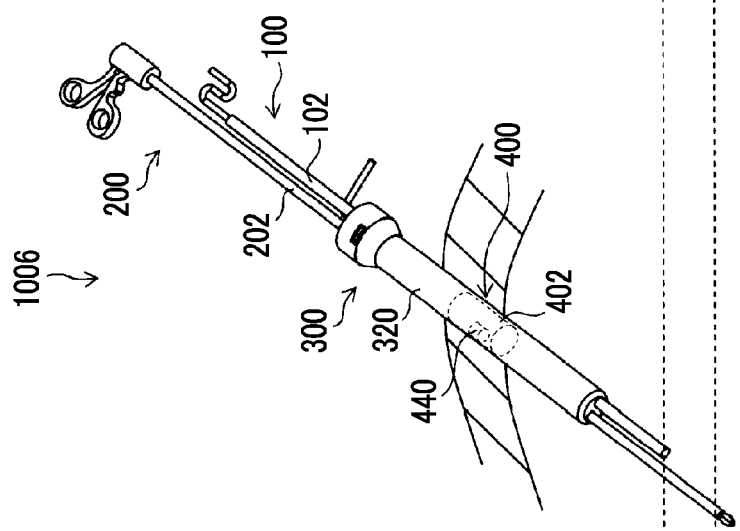

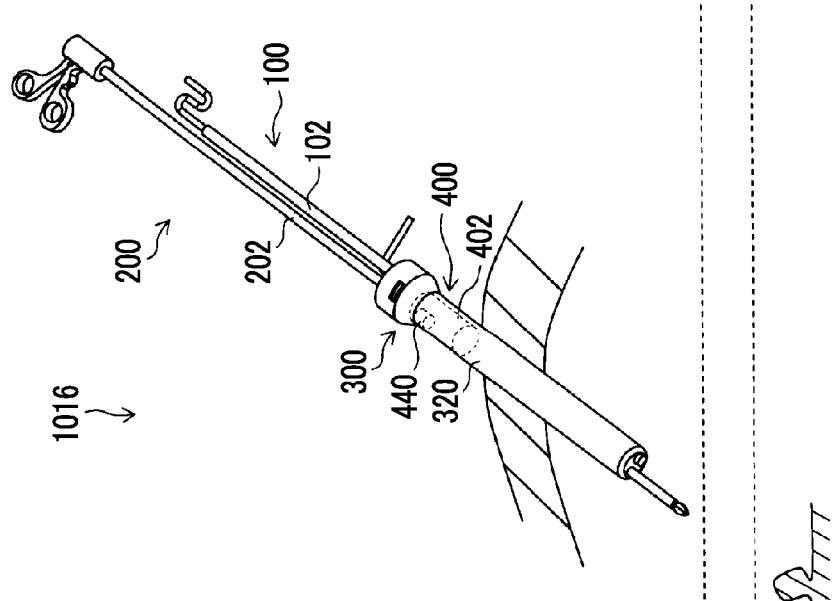
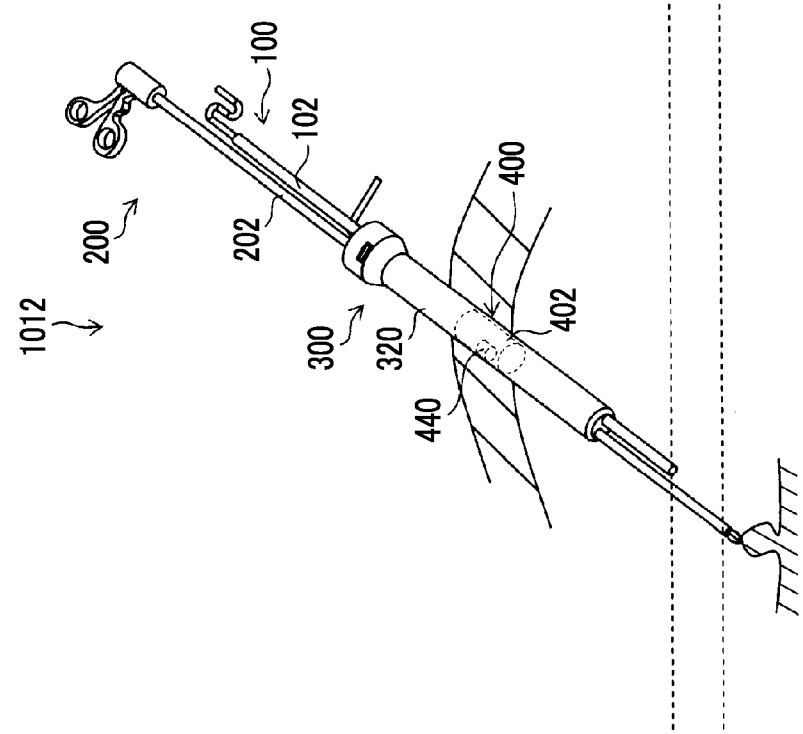

OPTICAL UNIT AND ENDOSCOPE

CROSS-REFERENCE TO RELATED APPLICATIONS

This application is a Continuation of PCT International Application No. PCT/JP2016/058007 filed on Mar. 14, 2016, which claims priority under 35 U.S.C. § 119(a) to Japanese Patent Application No. 2015-071818 filed on Mar. 31, 2015. Each of the above applications is hereby expressly incorporated by reference, in their entirety, into the present application.

BACKGROUND OF THE INVENTION

1. Field of the Invention

The present invention relates to an optical unit and an endoscope, and particularly, to an optical unit and an endoscope including a cover glass and an optical lens disposed at a distal end of an insertion part of the endoscope.

2. Description of the Related Art

As disclosed in JP2000-139821A and JP2000-217775A, an optical unit having a cover glass and an optical lens is provided at a distal end of an insertion part of an endoscope, and an image of an affected area, which enters an incidence surface of the cover glass and leaves an emission surface, is guided to an imaging device via the optical lens.

In the optical unit of JP2000-139821A and JP2000-217775A, the cover glass is attached to a distal end of a tubular holding tube. In this holding tube, a cover glass fixing part that fixes a side surface of the cover glass, a cover glass position restricting part that restricts the position of the cover glass in an optical axis direction, and an optical lens position restricting part that restricts the position of the optical lens in the optical axis direction are integrally configured.

Additionally, JP2000-139821A describes providing a coating surface on the side surface (an outer peripheral surface) of the cover glass. This coating surface is constituted of a low-reflection layer made of a chromic oxide layer ($Cr_2O_3$) constituting a lowermost layer, that is, a foundation layer that is vapor-deposited and formed on the side surface of the cover glass, and a nickel-plated layer that is superimposed on the low-reflection layer to constitute a joining layer of an uppermost layer. According to JP2000-139821A, a light beam, which enters the cover glass and reaches the low-reflection layer vapor-deposited on the outer peripheral surface of this cover glass, is hardly reflected by the low-reflection layer. Additionally, the side surface of the cover glass is joined to an inner peripheral surface of a metallic frame, which is the holding tube, with solder via the nickel-plated layer.

Meanwhile, a circumference groove serving as a filling chamber filled with a steam impermeable substance is formed on the side surface (outer peripheral surface) of the cover glass of JP2000-217775A. Additionally, a through-hole for filling the circumference groove with the steam impermeable substance therethrough is formed on a cover glass frame that is the holding tube. That is, JP2000-217775A describes the contents in which the circumference groove is formed on the side surface of the cover glass and the circumference groove is filled with the steam impermeable substance from the through-hole of the cover glass frame.

The optical unit of Patent JP2000-139821A and JP2000-217775A is adapted to enhance the airtightness between the side surface of the cover glass and the frame so as to be capable of withstanding autoclave sterilization treatment of the endoscope with high-pressure high-temperature steam. Thus, in JP2000-139821A, joining performance with the frame is enhanced by plating the side surface of the cover glass, and in JP2000-217775A, joining performance with the frame is enhanced by forming the circumference groove in the side surface of the cover glass and by filling the circumference groove with the steam impermeable substance.

SUMMARY OF THE INVENTION

Meanwhile, in order to further enhance the airtightness between the holding tube and the cover glass, it is not enough only to pour a melted joining member between the side surface of the cover glass and the inner peripheral surface of the holding tube.

Therefore, the optical unit of JP2000-139821A and JP2000-217775A has a problem that it is difficult to further enhance the airtightness between the holding tube and the cover glass.

It is considered that the problem can be solved by spacing and disposing the cover glass away from a position restricting part of the cover glass of the holding tube, a space (hereinafter referred to as a solder pool part) where the joining member is pooled is formed between the position restricting part of the cover glass and an outer peripheral edge part on a light emission surface side of the cover glass, and pouring the joining member into the solder pool part.

However, in this form, the position of the outer peripheral edge part of the cover glass on the light emission surface side is not restricted by the position restricting part of the cover glass of the holding tube. Therefore, there is a problem that the attachment accuracy of the cover glass with respect to the holding tube decreases and the airtightness decreases. Additionally, in a case where an optical lens capable of wide-angle shooting (for example, 120 degrees or more) is adopted, a distal end surface of the optical lens should be accurately disposed in close proximity to the emission surface of the cover glass such that a distal end of the holding tube is not projected on the imaging device. In this case, there also is a problem that the joining member poured into the solder pool part flows into the distal end surface of the optical lens.

Additionally, in a case where the optical unit is applied to a wide-angle optical lens which has a small diameter and in which the diameter of the cover glass is not large, the cover glass and the optical lens with power should be accurately and closely disposed at positions very close to each other in a state where the cover glass and the optical lens are kept parallel to each other.

The invention has been made in view of such circumstances, and an object thereof is to provide an optical unit and an endoscope that can enhance the airtightness between a holding tube and a cover glass without a joining member flowing into a distal end surface of an optical lens while maintaining the attachment accuracy of the cover glass and can secure a small diameter and a wide angle visual field.

In order to achieve the object of the invention, one aspect of the invention provides an optical unit having a distal end, a proximal end, and an optical axis in a first axial direction. The optical unit comprises a cover glass having an incidence surface on the distal end side, an emission surface on the proximal end side, and a side surface; an optical lens disposed on the emission surface side of the cover glass; a holding tube having a cover glass fixing part that fixes the side surface of the cover glass, a cover glass position restricting part that restricts a position of the cover glass in the first axial direction, and an optical lens position restricting part that restricts a position of the optical lens in the first axial direction; and a spacer that is disposed between the cover glass and the cover glass position restricting part, has a first end surface and a second end surface at both ends thereof in the first axial direction, and has a window part serving as an optical channel in the first axial direction between the first end surface and the second end surface. The first end surface is a surface disposed on the cover glass side, an external diameter of the first end surface being smaller than an internal diameter of the cover glass fixing part, and an antireflection treatment layer is provided on at least the first end surface.

According to the one aspect of the invention, the spacer having the window part serving as an optical channel is disposed between the cover glass position restricting part of the holding tube and the cover glass. The position of the cover glass in the first axial direction is restricted by the cover glass position restricting part via the spacer. Therefore, the attachment accuracy of the cover glass with respect to the holding tube can be maintained. Additionally, the external diameter of the first end surface of the spacer disposed on the cover glass side is smaller than the internal diameter of the cover glass fixing part of the holding tube. Accordingly, the solder pool part is provided in a region, which is surrounded by the side surface of the spacer, the cover glass fixing part, and the cover glass position restricting part, is formed. Since the joining member poured from the incidence surface side of the cover glass toward the solder pool part is dammed by the side surface of the spacer, the joining member does not flow into the distal end surface of the optical lens. Additionally, the side surface of the cover glass and the cover glass fixing part are joined together with the poured joining member, and an outer peripheral edge part of the emission surface of the cover glass is anchored to the holding tube with the joining member poured into the solder pool part.

Hence, according to the one aspect of the optical unit of the invention, the airtightness between the holding tube and the cover glass can be enhanced without the joining member flowing into the distal end surface of the optical lens while maintaining the attachment accuracy of the cover glass with respect to the holding tube.

Additionally, since at least the first end surface of the spacer includes the antireflection treatment layer, a light beam that has reached the antireflection treatment layer is hardly reflected. Accordingly, generation of flare can be suppressed.

Moreover, a spacer with a thickness corresponding to the angle of view of the optical lens can be selected and used for the optical unit. That is, the spacing between the cover glass and the optical lens can be accurately adjusted by adjusting the thickness of the spacer.

In one aspect of the invention, it is preferable that the holding tube includes a first recess that has a first inner wall surface and a first bottom surface and accommodates the cover glass, and a second recess that has a second inner wall surface and a second bottom surface, is open to the first bottom surface of the first recess, and accommodates the spacer, the first inner wall surface is provided at a position that faces the side surface of the cover glass and has the cover glass fixing part, the second bottom surface is provided at a position that faces the second end surface of the spacer and has the cover glass position restricting part, an internal diameter of the second inner wall surface is made smaller than an internal diameter of the first inner wall surface, and a depth of the second recess in the first axial direction is made smaller than a thickness of the spacer in the first axial direction, and a solder pool part is provided in a region surrounded by the first recess, the cover glass, and the spacer.

According to the one aspect of the invention, the cover glass is accommodated in the first recess having the first inner wall surface and the first bottom surface with respect to the holding tube. The spacer is accommodated in the second recess having the second inner wall surface and the second bottom surface with respect to the holding tube. The second recess is open to the first bottom surface. Additionally, the first inner wall surface has the cover glass fixing part, and the second bottom surface has the cover glass position restricting part.

In the above aspect, the internal diameter of the second inner wall surface is made smaller than the internal diameter of the first inner wall surface, and the depth of the second recess in the first axial direction is made smaller than the thickness of the spacer in the first axial direction. Therefore, the solder pool part can be provided in the region surrounded by the first recess, the side surface of the cover glass, and the side surface of the spacer.

In one aspect of the invention, it is preferable that the holding tube has a third inner wall surface and a third bottom surface and has a third recess that accommodates the cover glass and the spacer, the third inner wall surface is provided at a position that faces the side surface of the cover glass, and has the cover glass fixing part, the third bottom surface is provided at a position that faces the second end surface of the spacer, and has the cover glass position restricting part, and the spacer has a stepped part configured such that the external diameter of the first end surface is smaller than an external diameter of the second end surface, and a solder pool part is provided between the third inner wall surface and the stepped part.

According to the one aspect of the invention, the cover glass is accommodated in the third recess having the third inner wall surface and the third bottom surface with respect to the holding tube. Additionally, the third inner wall surface has the cover glass fixing part, and the third bottom surface has the cover glass position restricting part.

In the above aspect, the spacer has the stepped part in which the external diameter of the first end surface is made smaller than the external diameter of the second end surface. Therefore, the solder pool part can be provided in the region surrounded by the third inner wall surface and the stepped part.

In one aspect of the invention, it is preferable that a metallized layer is formed on the side surface of the cover glass, and a plated layer is formed on the cover glass fixing part.

According to the one aspect of the invention, the cover glass made of glass can be airtightly joined to the holding tube made of metal with the joining member.

In one aspect of the invention, it is preferable that a reflectivity of the antireflection treatment layer of the spacer is 10% or less.

According to the one aspect of the invention, generation of flare can be sufficiently suppressed.

In one aspect of the invention, it is preferable that the window part has a through-hole that allows a first opening part formed on the first end surface and the second opening part formed on the second end surface to communicate with each other, and an opening diameter of the first opening part is made smaller than an opening diameter of the second opening part, and the through-hole has a tapered inner peripheral surface of which an internal diameter becomes gradually smaller from the second end surface toward the first opening part side.

According to the one aspect of the invention, since the tapered inner peripheral surface does not face the emission surface of the cover glass, the flare generated by the light emitted from the emission surface of the cover glass being reflected by the tapered inner peripheral surface can be suppressed.

In one aspect of the invention, it is preferable that, when a direction perpendicular to the first axial direction is defined as a second axial direction and a direction perpendicular to the first axial direction and the second axial direction is defined as a third axial direction, the cover glass fixing part restricts positions of the cover glass in the second axial direction and the third axial direction.

According to the one aspect of the invention, the positions of the cover glass in the second axial direction and the third axial direction are restricted by the cover glass fixing part, respectively.

In order to achieve the object of the invention, one aspect of the invention provides an endoscope comprising: an insertion part inserted into the body; and an optical unit that is provided at a distal end part of the insertion part and has a distal end, a proximal end, and an optical axis in a first axial direction. The optical unit includes a cover glass having an incidence surface on the distal end side, an emission surface on the proximal end side, and a side surface, an optical lens disposed on the emission surface side of the cover glass, a holding tube having a cover glass fixing part that fixes the side surface of the cover glass, a cover glass position restricting part that restricts a position of the cover glass in the first axial direction, and an optical lens position restricting part that restricts a position of the optical lens in the first axial direction, and a spacer that is disposed between the cover glass and the cover glass position restricting part, has a first end surface and a second end surface at both ends thereof in the first axial direction, and has a window part serving as an optical channel in the first axial direction between the first end surface and the second end surface. The first end surface is a surface disposed on the cover glass side, an external diameter of the first end surface being smaller than an internal diameter of the cover glass fixing part, and an antireflection treatment layer is provided on at least the first end surface.

According to the one aspect of the endoscope of the invention, the airtightness between the holding tube and the cover glass can be enhanced without the joining member flowing into the distal end surface of the optical lens while maintaining the attachment accuracy of the cover glass with respect to the holding tube.

Additionally, since at least the first end surface of the spacer includes the antireflection treatment layer, a light beam that has reached the antireflection treatment layer is hardly reflected. Accordingly, generation of flare can be suppressed.

In a case where the optical unit of the invention is applied to a wide-angle optical lens which has a small diameter and in which the diameter of the cover glass is not large, the cover glass and the optical lens with power should be closely disposed at positions very close to each other in a state where the cover glass and the optical lens are kept parallel to each other.

Thus, according to the one aspect of the invention, by using a spacer with a small thickness, the cover glass and the optical lens can be accurately and closely disposed while being made parallel to each other by the spacer. Therefore, according to the one aspect of the invention, the optical unit and the endoscope with a small diameter and a wide angle visual field can be provided.

According to the optical unit and the endoscope of the invention, the airtightness between the holding tube and the cover glass can be enhanced without the joining member flowing into the distal end surface of the optical lens while maintaining the attachment accuracy of the cover glass and a small diameter and a wide angle visual field can be secured.

BRIEF DESCRIPTION OF THE DRAWINGS

FIG. 10 is an enlarged cross-sectional view illustrating a portion of FIG. 9.

FIGS. 12A and 12B are views illustrating a state when a treatment tool insertion part is pushed into an affected area side within a body cavity from the near side, FIG. 12A illustrates a state before the treatment tool insertion part is pushed, and FIG. 12B illustrates a state after the treatment tool insertion part is pushed.

FIGS. 13A and 13B are views illustrating a state when the treatment tool insertion part is pushed into the affected area side within the body cavity from the near side, FIG. 13A illustrates a state before the treatment tool insertion part is pushed, and FIG. 13B illustrates a state after the treatment tool insertion part is pushed.

FIG. 14A illustrates a state before the treatment tool insertion part is pulled, and FIG. 14B illustrates a state after the treatment tool insertion part is pulled.

FIGS. 15A and 15B are views illustrating a state when the treatment tool insertion part is pulled from the affected area side within a body cavity to the near side, FIG. 15A illustrates a state before the treatment tool insertion part is pulled, and FIG. 15B illustrates a state after the treatment tool insertion part is pulled.

DESCRIPTION OF THE PREFERRED EMBODIMENTS

Hereinafter, preferable embodiments of an optical unit and an endoscope related to the invention will be described according to the accompanying drawings.

Figure 1:
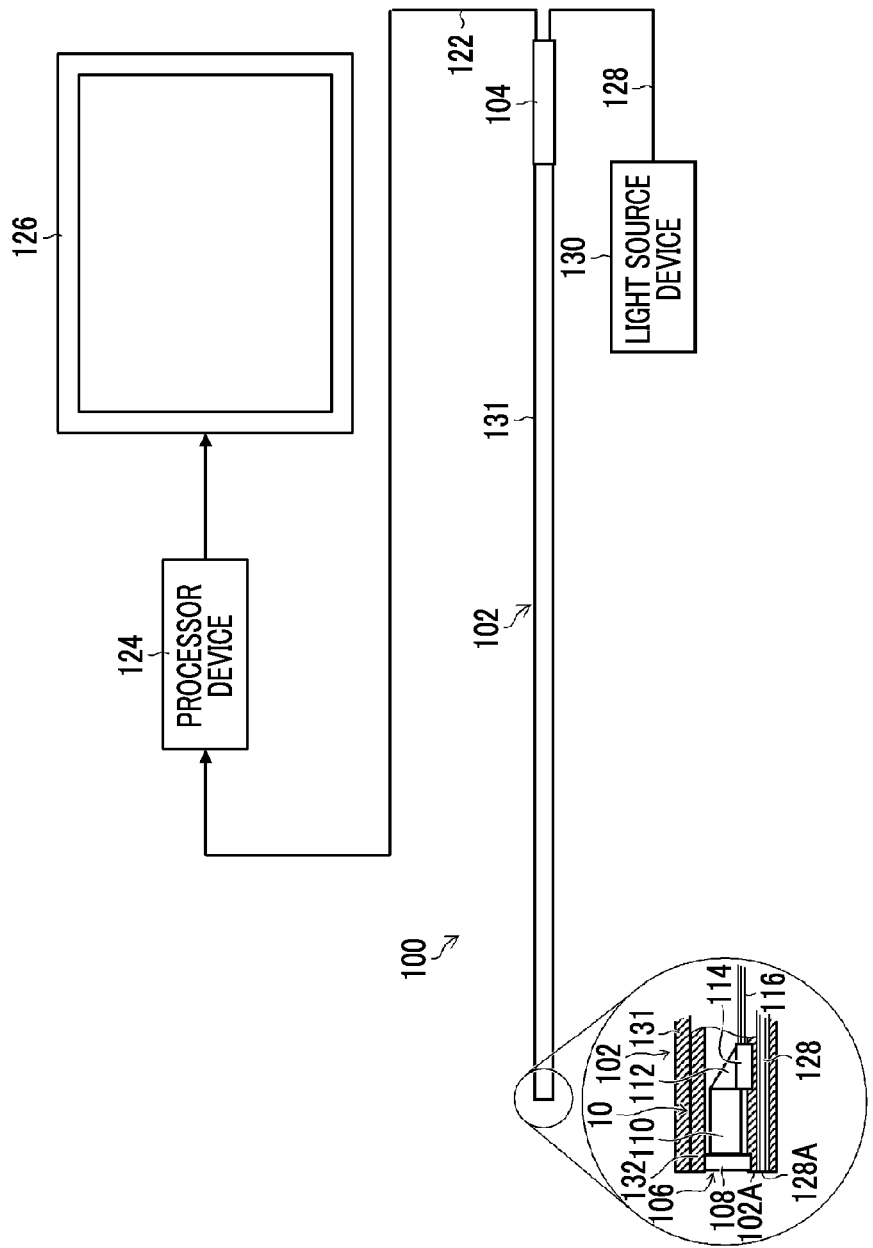
FIG. 1 is a configuration view of an endoscope equipped with an optical unit of an embodiment.

[Endoscope 100] FIG. 1 is a configuration view of an endoscope 100 of an embodiment provided with an optical unit 10 of a first embodiment, and illustrates a direct viewing type hard endoscope, such as a laparoscope, as the endoscope 100.

Figure 2:
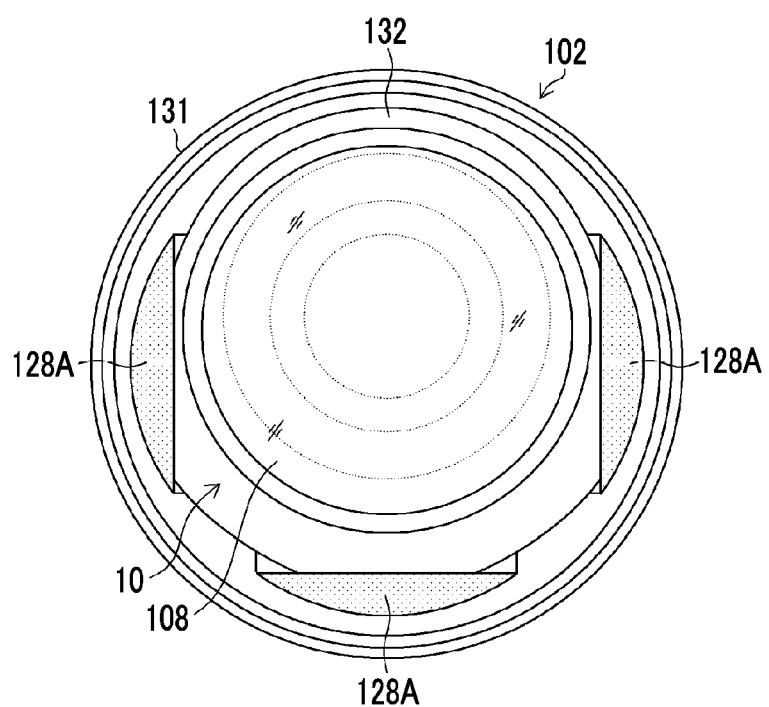
FIG. 2 is a front view of a distal end surface of an insertion part of the endoscope.

The endoscope 100 includes a cylindrical insertion part 102 inserted into a patient's body, and a cylindrical operating part 104 connected to a proximal end of the insertion part 102. FIG. 2 is a front view of a distal end surface 102A of the insertion part 102.

As illustrated in FIGS. 1 and 2, a cover glass 108, which constitutes a distal end of an optical member 106, is disposed on the distal end surface 102A of the insertion part 102. Additionally, as illustrated in an enlarged cross-sectional view of some main parts in FIG. 1, an optical lens 110, which constitutes a main body of the optical member 106, and a prism 112 are built inside the insertion part 102. Additionally, an imaging device 114, which picks up an observation image obtained through the optical member 106, and a plurality of signal lines 116, which have their distal ends connected to the imaging device 114 and transmit image signals output from the imaging device 114, are built inside the insertion part 102.

Proximal ends of the signal lines 116 are connected to a distal end of a terminal part (not illustrated) inside the insertion part 102. A distal end of a signal line 122 is connected to a proximal end of this terminal part, the signal line 122 extends from the insertion part 102 via the operating part 104 to the outside, and a proximal end of the signal line 122 is connected to a processor device 124.

As the imaging device 114, a charge coupled device (CCD) type image sensor or a complementary metal oxide semiconductor (CMOS) image sensor can be used.

The processor device 124 receives the image signals output via the signal lines 116 and the signal line 122 from the imaging device 114 to generate video signals, and outputs the video signals to a monitor 126. Accordingly, an image on the inside of the body is displayed on the monitor 126.

Additionally, a plurality of optical fiber element wires 128, which are optical transmission members, are built inside the insertion part 102.

Proximal ends of the optical fiber element wires 128 extend from the insertion part 102 via the operating part 104 to the outside and are connected to a light source device 130. Accordingly, the light from the light source device 130 is supplied to the optical fiber element wires 128 and is irradiated from light emission end surfaces 128A of the optical fiber element wires 128, which are exposed to the distal end surface 102A of the insertion part 102, to the outside.

In a surgery using the endoscope 100, an affected area is irradiated with light of an opening angle of 120 degrees or more from the light emission end surfaces 128A of the optical fiber element wires 128. The irradiated affected area is imaged by the imaging device 114 via the optical member 106, and an operator operates a treatment tool (not illustrated) to perform treatment of the affected area while confirming the video through the monitor 126.

[Optical Unit 10 of First Embodiment]

Figure 3:
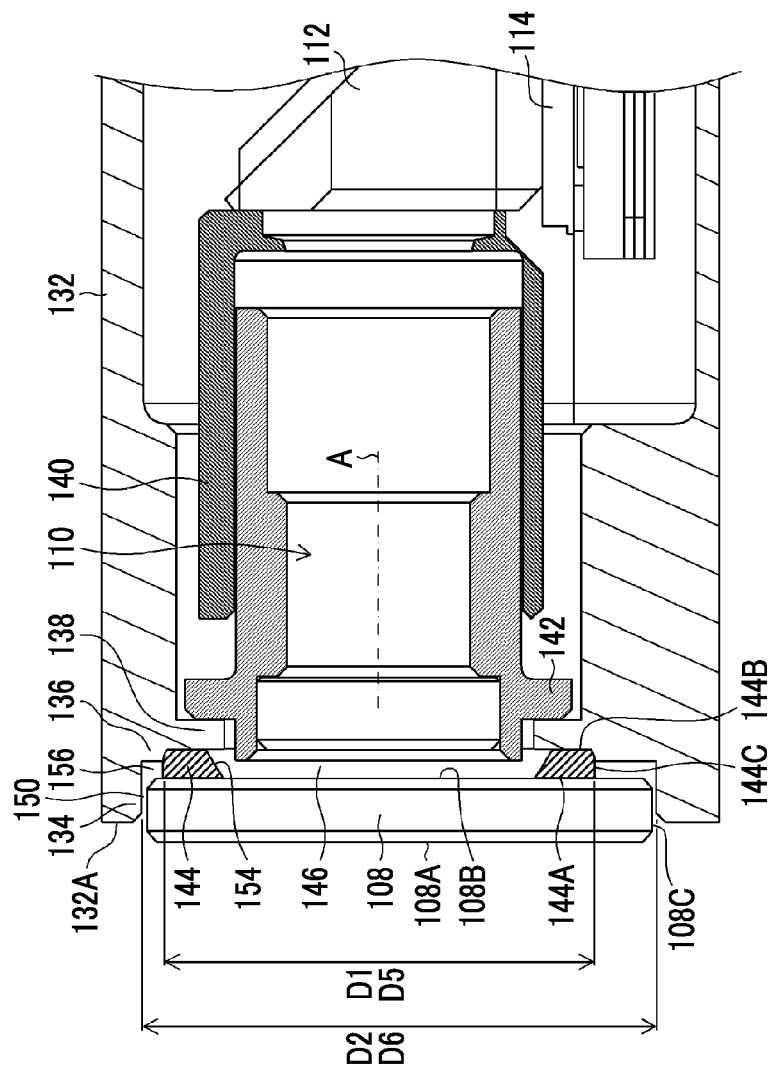
FIG. 3 is a cross-sectional view illustrating the structure of an optical unit of a first embodiment.
Figure 4:
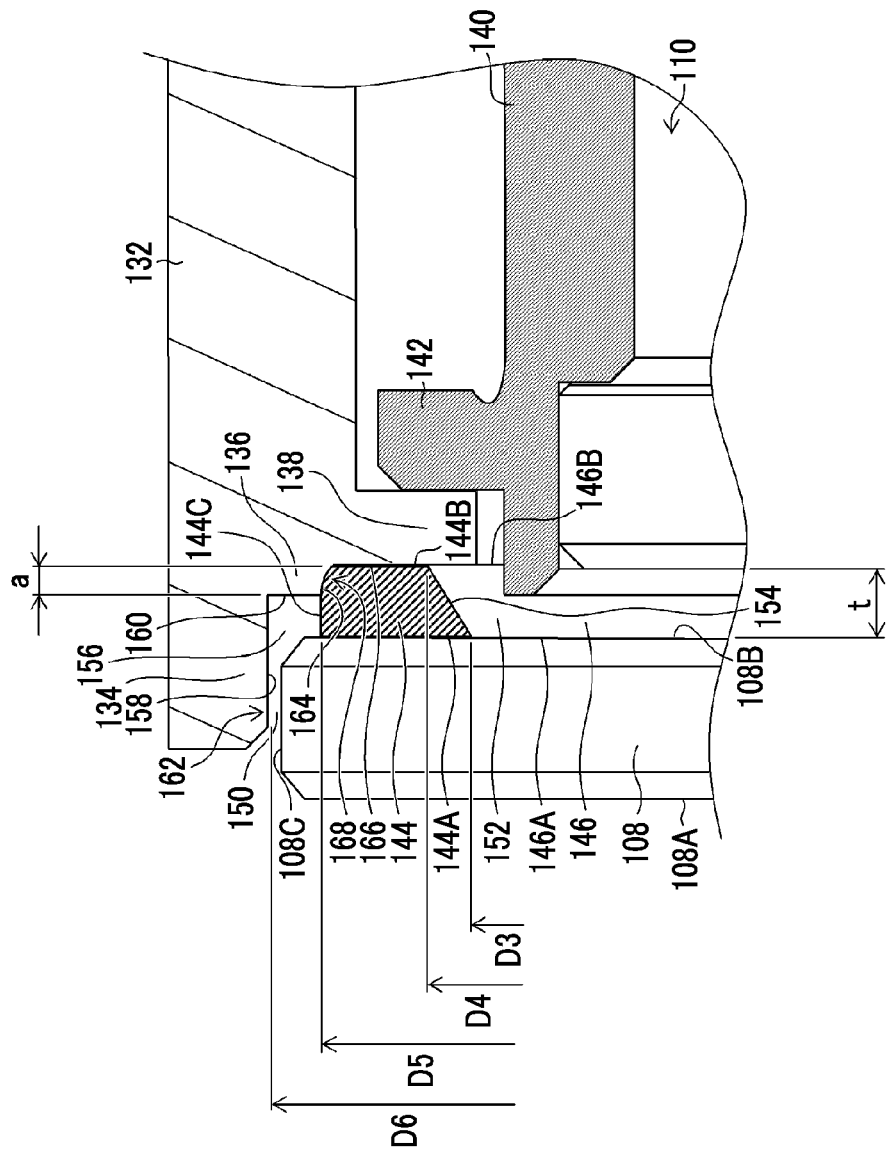
FIG. 4 is an enlarged cross-sectional view of main parts of the optical unit illustrated in FIG. 3.

FIG. 3 is a cross-sectional view illustrating the structure of the optical unit 10 of the first embodiment disposed at the distal end of the insertion part 102. Additionally, FIG. 4 is an enlarged cross-sectional view of main parts of FIG. 3.

The optical unit 10 is provided at a distal end of a holding tube 132 disposed inside an outer tube 131 (refer to FIG. 1) of the insertion part 102. The optical fiber element wires 128 are disposed in a gap between the outer tube 131 and the holding tube 132, and as illustrated in FIG. 2, are disposed in three places along the periphery of the cover glass 108.

The holding tube 132 of FIG. 3 has a tubular shape, the inside of which is hollow, and an opening of a distal end 132A is airtightly sealed by the disk-like cover glass 108 that is a parallel planar plate.

The optical unit 10 has a distal end, a proximal end, and an optical axis in a first axial direction indicated by reference sign A.

Additionally, the optical unit 10 includes the cover glass 108 having an incidence surface 108A on a distal end side and an emission surface 108B and a side surface 108C on a proximal end side, and the optical lens 110 disposed on the emission surface 108B side of the cover glass 108.

Additionally, the optical unit 10 includes the holding tube 132. An inner peripheral surface of the holding tube 132 is provided with a cover glass fixing part 134 that fixes the side surface 108C of the cover glass 108, a cover glass position restricting part 136 that restricts the position of the cover glass 108 in the first axial direction indicated by reference sign A, and an optical lens position restricting part 138 that restricts the position of the optical lens 110 in the first axial direction.

The optical lens 110 is configured such that a plurality of lenses installed side by side in the first axial direction are held by a lens barrel 140. The optical lens 110 is accurately positioned by the holding tube 132 by a distal end flange part 142 of the lens barrel 140 abutting against the optical lens position restricting part 138 in the first axial direction.

Moreover, the optical unit 10 includes a ring-shaped spacer 144 disposed between the cover glass 108 and the cover glass position restricting part 136. The spacer 144 has a first end surface 144A, a second end surface 144B, and a side surface 144C at both ends in the first axial direction, and has a window part 146 that serves as an optical channel in the first axial direction between the first end surface 144A and the second end surface 144B. The first end surface 144A is a surface that is disposed on the cover glass 108 side and abuts against the emission surface 108B of the cover glass 108, and an external diameter D1 of the first end surface 144A is smaller than an internal diameter D2 of the cover glass fixing part 134.

Figure 5:
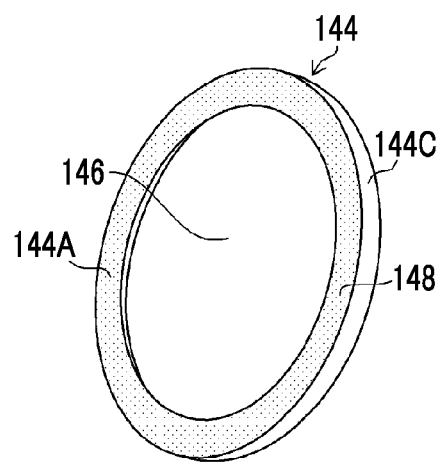
FIG. 5 is a perspective view of a spacer of the optical unit illustrated in FIG. 3.

FIG. 5 is a perspective view of the spacer 144. As illustrated in this drawing, the spacer 144 has an antireflection treatment layer 148 at least on the first end surface 144A. That is, the antireflection treatment layer 148 is not limited to the first end surface 144A, and may be provided on the second end surface 144B or the side surface 144C.

Additionally, as illustrated in FIG. 4, a gap 150 is provided between the side surface 108C of the cover glass 108 and the cover glass fixing part 134, and a joining member, such as solder, is poured into the gap 150 from the outside of the optical unit 10. The side surface 108C of the cover glass 108 is airtightly joined to the cover glass fixing part 134 with this solder.

In this case, it is preferable to form a metallized layer on the side surface 108C of the cover glass 108 and to form a plated layer on the surface of the cover glass fixing part 134.

Accordingly, for example, the cover glass 108 made of glass can be airtightly joined to the holding tube 132 made of metal with solder.

Additionally, the reflectivity of the antireflection treatment layer 148 of the spacer 144 is preferably 30% or less, more preferably 10% or less, and still more preferably 5% or less.

Accordingly, generation of the flare originating from the light, which is incident via the cover glass 108, can be sufficiently suppressed.

Moreover, the window part 146 of the spacer 144 has a through-hole 152 that allows a first opening part 146A formed on the first end surface 144A and a second opening part 146B formed on the second end surface 144B to communicate with each other. In the through-hole 152, an opening diameter D3 of the first opening part 146A is made smaller than an opening diameter D4 of the second opening part 146B, and the through-hole 152 has a tapered inner peripheral surface 154 of which the internal diameter becomes gradually smaller from the second end surface 144B toward the first opening part 146A side.

Accordingly, since the tapered inner peripheral surface 154 does not face the emission surface 108B of the cover glass 108, the flare generated by the light emitted from the emission surface 108B of the cover glass 108 being reflected by the tapered inner peripheral surface 154 can be suppressed.

Moreover, in FIG. 3, when a direction perpendicular to the first axial direction indicated by reference sign A is defined as a second axial direction and a direction perpendicular to the first axial direction and the second axial direction is defined as a third axial direction, it is preferable that the cover glass fixing part 134 restricts the positions of the cover glass 108 in the second axial direction and the third axial direction.

Accordingly, the cover glass 108 is restricted in position in the second axial direction and the third axial direction, respectively, by the cover glass fixing part 134 and is positioned by the holding tube 132.

[Feature of Optical Unit 10]

In the optical unit 10, the spacer 144 having the window part 146 serving as an optical channel is disposed between the cover glass position restricting part 136 of the holding tube 132 and the cover glass 108. The position of the cover glass 108 in the first axial direction indicated by reference sign A is restricted by the cover glass position restricting part 136 via the spacer 144. Therefore, the attachment accuracy of the cover glass 108 with respect to the holding tube 132 can be maintained.

Additionally, the external diameter D1 of the first end surface 144A of the spacer 144 disposed on the cover glass 108 side is smaller than the internal diameter D2 of the cover glass fixing part 134 of the holding tube 132. Accordingly, a region 156, which is surrounded by the side surface 144C of the spacer 144, the cover glass fixing part 134, and the cover glass position restricting part 136, is formed, and a solder pool part is provided in the region 156. Otherwise, the entire region 156 is used as the solder pool part.

Accordingly, since the solder poured from the incidence surface 108A side of the cover glass 108 via the gap 150 toward the solder pool part of the region 156 is dammed by the side surface 144C of the spacer 144, the solder does not flow into a distal end surface of the optical lens 110.

Additionally, the side surface 108C of the cover glass 108 and the cover glass fixing part 134 are joined together with the poured solder, and an outer peripheral edge part of the emission surface 108B of the cover glass 108 is anchored to the holding tube 132 with the solder poured into the solder pool part.

Hence, according to the optical unit 10 of the first embodiment, the airtightness between the holding tube 132 and the cover glass 108 can be enhanced without solder flowing into the distal end surface of the optical lens 110 while maintaining the attachment accuracy of the cover glass 108 with respect to the holding tube 132.

Additionally, in order to provide an optical unit with a small diameter and a wide angle visual field (for example, 120 degrees or more), a plurality of the spacers 144 with different thicknesses in the first axial direction are prepared, and a spacer 144 of the thickness corresponding to the angle of view of the optical lens 110 is selected and used for the optical unit 10.

For example, in a case where the holding tube 132 is applied to a wide-angle optical lens 110 which has a small diameter and in which the diameter of the cover glass 108 is not large, the cover glass 108 and the optical lens 110 with power should be accurately and closely disposed at positions very close to each other in a state where the cover glass 108 and the optical lens 110 are kept parallel to each other.

Thus, by selecting and using a spacer 144 with a small thickness, the cover glass 108 and the optical lens 110 can be closely disposed while being made parallel to each other by the spacer 144. Therefore, the optical unit 10 with a small diameter and a wide angle visual field can be provided, and the endoscope 100 on which the optical unit 10 is mounted can be provided.

[Detailed Structure of Optical Unit 10]

As illustrated in FIG. 4, the holding tube 132 includes a first recess 162 and a second recess 168. The first recess 162 has a first inner wall surface 158 and a first bottom surface 160, and accommodates the side surface 108C of the cover glass 108. The second recess 168 has a second inner wall surface 164 and a second bottom surface 166, is open to the first bottom surface 160 of the first recess 162, and accommodates an outer peripheral part of the spacer 144.

The first inner wall surface 158 is provided at a position that faces the side surface 108O of the cover glass 108, and has the cover glass fixing part 134. The second bottom surface 166 is provided at a position that faces the second end surface 144B of the spacer 144, and has the cover glass position restricting part 136. An internal diameter D5 of the second inner wall surface 164 substantially equal to the external diameter D1 (refer to FIG. 3) of the first end surface 144A of the spacer 144 is smaller than an internal diameter D6 of the first inner wall surface 158 substantially equal to the internal diameter D2 (refer to FIG. 3) of the cover glass fixing part 134. Additionally, a depth of the second recess 168 in the first axial direction is made smaller than a thickness t of the spacer 144 in the first axial direction. Accordingly, the region 156 surrounded by the first recess 162, the cover glass 108, and the spacer 144 includes the solder pool part as mentioned earlier.

According to the above structure of the optical unit 10, the cover glass 108 is accommodated in the first recess 162 having the first inner wall surface 158 and the first bottom surface 160 with respect to the holding tube 132. The spacer 144 is accommodated in the second recess 168 having the second inner wall surface 164 and the second bottom surface 166 with respect to the holding tube 132.

In the above structure, the internal diameter D5 of the second inner wall surface 164 is made smaller than the internal diameter D6 of the first inner wall surface 158, and the depth of the second recess 168 in the first axial direction is made smaller than the thickness t of the spacer 144 in the first axial direction. Thus, the solder pool part can be provided in the region 156 surrounded by the first recess 162, the side surface 108C of the cover glass 108, and the side surface 144C of the spacer 144.

[Optical unit 170 of Second Embodiment]

Figure 6:
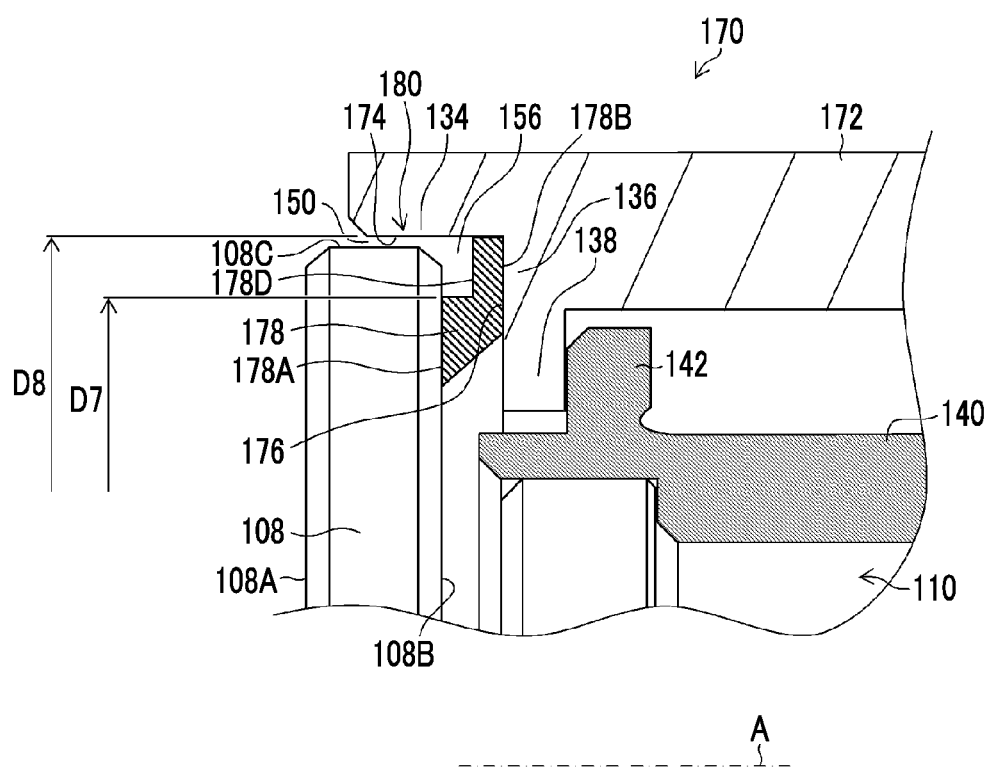
FIG. 6 is an enlarged cross-sectional view of main parts illustrating the configuration of an optical unit of a second embodiment.

FIG. 6 is an enlarged cross-sectional view of main parts of illustrating the configuration of an optical unit 170 of a second embodiment. In addition, in a case where the optical unit 170 is described, members, which are the same as or similar to those of the optical unit 10 illustrated in FIGS. 1 to 5, will be designated by the same reference signs, and the description thereof will be omitted.

A holding tube 172 of the optical unit 170 includes a third recess 180 that has a third inner wall surface 174 and a third bottom surface 176 and that accommodates the cover glass 108 and a spacer 178.

The third inner wall surface 174 is provided at a position that faces the side surface 108C of the cover glass 108, and has the cover glass fixing part 134. The third bottom surface 176 is provided at a position that faces the second end surface 178B of the spacer 178, and has the cover glass position restricting part 136.

The spacer 178 has a stepped part 178D in which an external diameter D7 of a first end surface 178A is made smaller than an external diameter D8 of a second end surface 178B. The region 156 for providing the solder pool part between the third inner wall surface 174 and the stepped part 178D is formed in the spacer 178.

[Feature of Optical Unit 170]

According to the optical unit 170, the cover glass 108 is accommodated in the third recess 180 having the third inner wall surface 174 and the third bottom surface 176 with respect to the holding tube 172. Additionally, the third inner wall surface 174 has the cover glass fixing part 134, and the third bottom surface 176 has the cover glass position restricting part 136.

Moreover, in the optical unit 170, the spacer 178 is disposed between the cover glass position restricting part 136 of the holding tube 172 and the cover glass 108. The position of the cover glass 108 in the first axial direction indicated by reference sign A is restricted by the cover glass position restricting part 136 via the spacer 178. Therefore, the attachment accuracy of the cover glass 108 with respect to the holding tube 172 can be maintained.

Additionally, the spacer 178 has the stepped part 178D in which the external diameter D7 of the first end surface 178A is made smaller than the external diameter D8 of the second end surface 178B. Therefore, the solder pool part can be provided in the region 156 surrounded by the third inner wall surface 174 and the stepped part 178D.

Accordingly, since the solder poured from the incidence surface 108A side of the cover glass 108 via the gap 150 toward the solder pool part of the region 156 is dammed by the spacer 178, the solder does not flow into the distal end surface of the optical lens 110. Additionally, the side surface 108C of the cover glass 108 and the cover glass fixing part 134 are joined together with the poured solder, and the outer peripheral edge part of the emission surface 108B of the cover glass 108 is anchored to the holding tube 132 with the solder poured into the solder pool part.

Hence, according to the optical unit 170 of the second embodiment, the airtightness between the holding tube 172 and the cover glass 108 can be enhanced without solder flowing into the distal end surface of the optical lens 110 while maintaining the attachment accuracy of the cover glass 108 with respect to the holding tube 172. Additionally, an optical unit with a small diameter and a wide angle visual field can be achieved similar to the optical unit 10 of the first embodiment.

Although the optical units 10, 170 of the endoscope 100 related to the embodiments have been described above in detail, it is natural that the invention is not limited to the above embodiments, and various improvements and modifications may be made without departing from the scope of the invention.

Additionally, in the embodiments, the hard endoscope has been exemplified and described as the endoscope 100. However, the endoscope is not limited to the hard endoscope, and the invention can also be applied to a flexible endoscope in which an insertion part of an endoscope has a flexible part, a curved part, and a distal end rigid part.

[Usage Example of Endoscope 100]

Figure 7:
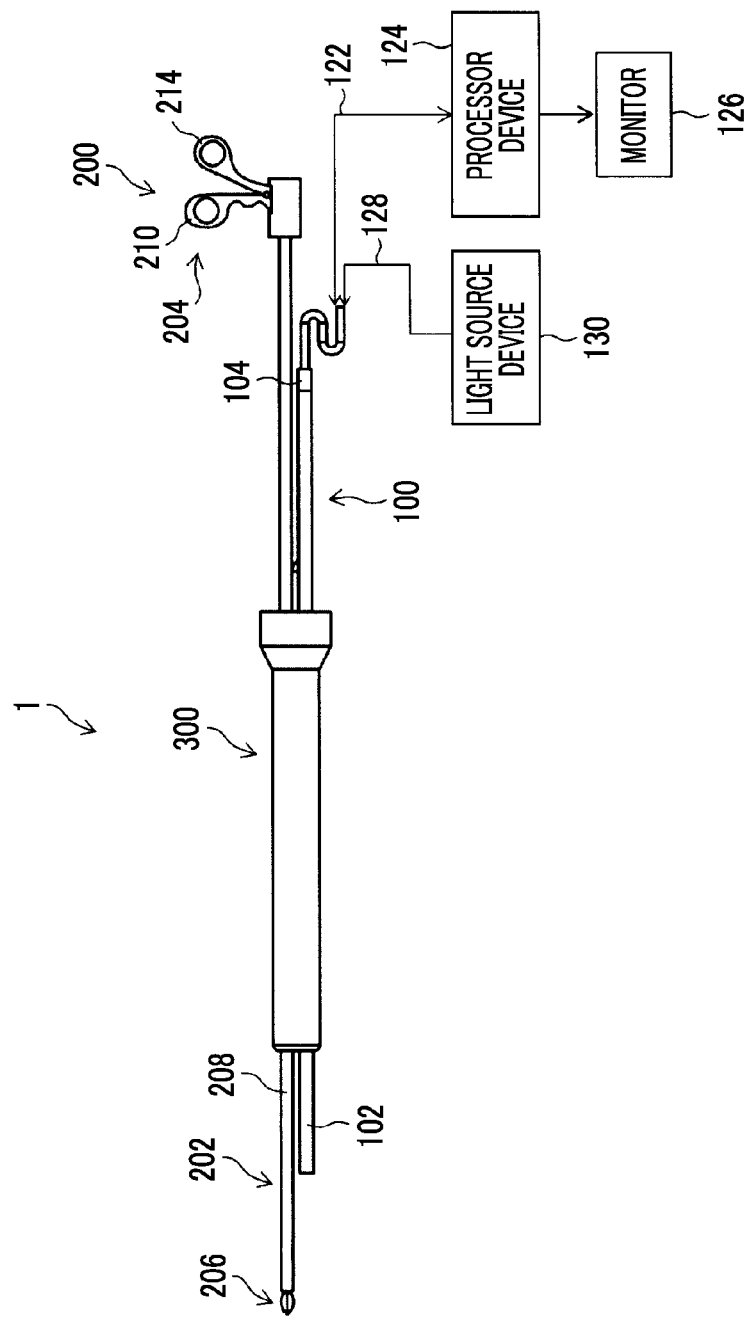
FIG. 7 is a schematic configuration view of an endoscopic surgical device related to the invention.

FIG. 7 is a schematic block diagram of the endoscope 100 applied to the endoscopic surgical device 1.

The endoscopic surgical device 1 includes an endoscope 100 that observes the inside of a patient's body cavity, a treatment tool 200 for examining or treating an affected area within the patient's body cavity, and an overtube 300 that guides the endoscope 100 and the treatment tool 200 into the body cavity.

As illustrated in FIG. 1, the treatment tool 200 consists of, for example, forceps, and includes an elongated treatment tool insertion part 202 that is inserted into a body cavity, an operating part 204 that is provided on the proximal end side of the treatment tool insertion part 202 and is gripped by an operator, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is coupled to the fixed handle 210 in a rotationally movable manner via a rotational movement pin. A proximal end part of the operating shaft is coupled to the movable handle 214.

The treatment part 206 is provided with a pair of gripping members that is openable and closable. The gripping members are coupled to a distal end part of the operating shaft via a driving mechanism (not illustrated). With the rotational movement operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, and an ultrasonic aspirator.

Figure 8:
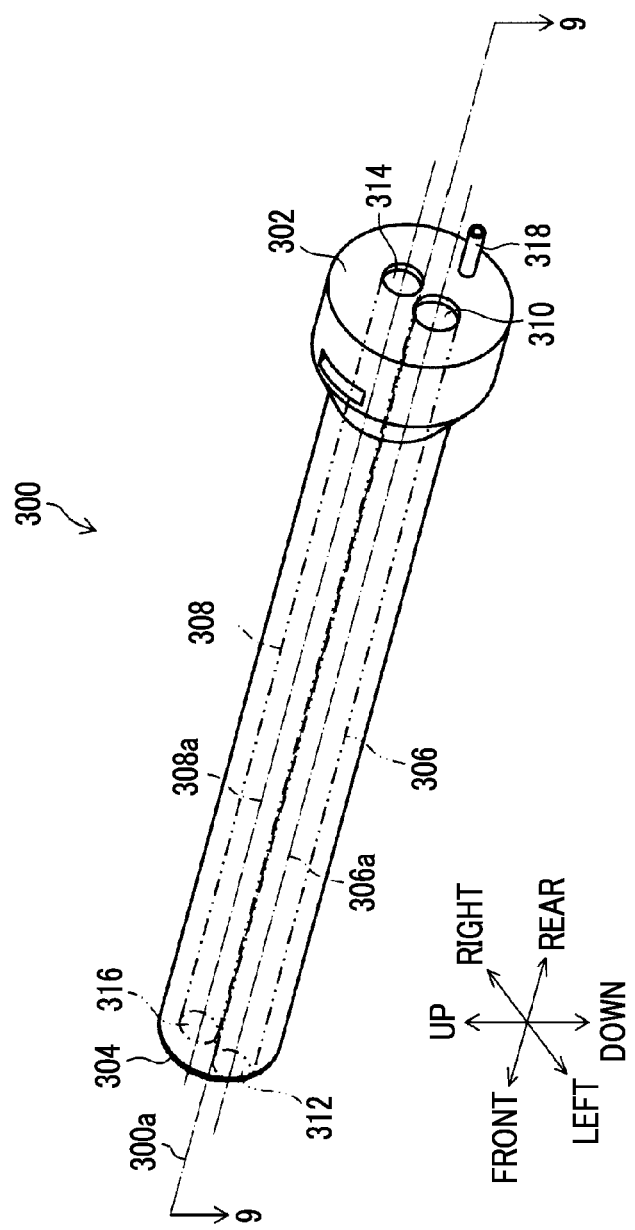
FIG. 8 is an external perspective view illustrating an overtube from the rear upper left direction.

FIG. 8 is an external perspective view illustrating the overtube 300 from the rear upper left direction.

The overtube 300 has an endoscope insertion passage 306 through which the insertion part 102 of the endoscope 100 is inserted so as to be movable backward and forward, and a treatment tool insertion passage 308 through which the treatment tool insertion part 202 of the treatment tool 200 is inserted so as to be movable backward and forward.

The endoscope insertion passage 306 has a diameter such that at least the insertion part 102 is insertable therethrough with an endoscope insertion axis 306a parallel to a reference axis 300a representing a central axis of the entire overtube 300 as a central axis, and has a space portion within the overtube 300, which passes through the overtube 300 from a proximal end surface 302 to a distal end surface 304. The endoscope insertion axis 306a is equivalent to the position of an axis of the insertion part 102 inserted through the endoscope insertion passage 306.

The proximal end surface 302 is provided with an endoscope insertion port 310 that allows the insertion part 102 to be inserted into the endoscope insertion passage 306 therethrough, and the distal end surface 304 is provided with an endoscope delivery port 312 that allows the insertion part 102 inserted into the endoscope insertion passage 306 to be delivered to the outside therethrough.

The treatment tool insertion passage 308 has a diameter such that at least the treatment tool insertion part 202 is insertable therethrough with a treatment tool insertion axis 308a parallel to the reference axis 300a as a central axis, and has a space portion within the overtube 300, which passes through the overtube 300 from the proximal end surface 302 to the distal end surface 304. The treatment tool insertion axis 308a is equivalent to the position of an axis of the treatment tool insertion part 202 inserted through the treatment tool insertion passage 308.

The proximal end surface 302 is provided with a treatment tool insertion port 314 that allows the treatment tool insertion part 202 to be inserted into the treatment tool insertion passage 308 therethrough, and the distal end surface 304 is provided with a treatment tool delivery port 316 that allows the treatment tool insertion part 202 inserted into the treatment tool insertion passage 308 to be delivered to the outside therethrough.

In addition, regarding the position and orientation of a space where the overtube 300 is disposed, terms called forward, backward, left, right, up, and down are used with the orientation from the proximal end surface 302 in a direction along the reference axis 300a to the distal end surface 304 defined as the forward and with the orientation from the reference axis 300a to the endoscope insertion axis 306a defined as the left.

Figure 9:
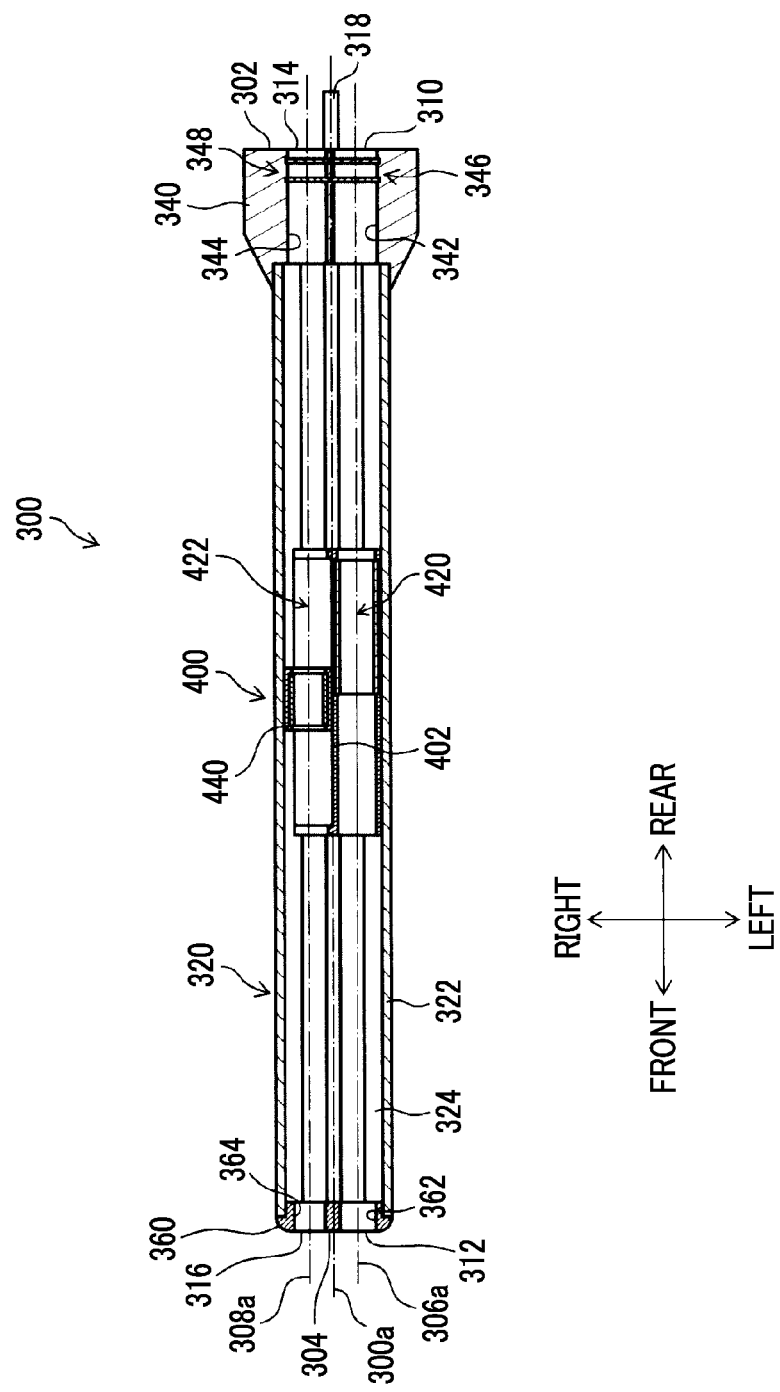
FIG. 9 is a cross-sectional view, taken along line 9-9 of FIG. 8, illustrating an internal structure of the overtube.

FIG. 9 is a cross-sectional view (a cross-sectional view taken along line 9-9 of FIG. 8) illustrating the internal structure of the overtube 300, and illustrates a cross-section cut in a plane that includes the reference axis 300a and is orthogonal to an upward-downward direction. In the present specification, a cross-sectional view simply refers to as a cross-sectional view taken along the same plane as that of FIG. 9.

The overtube 300 has an overtube body 320 that occupies the substantial entirety of the overtube in the forward-backward direction, a proximal end cap 340 disposed at a rear part of the overtube 300, a distal end cap 360 disposed at a distal end part of the overtube, and a slider 400 disposed inside the overtube 300.

The overtube body 320 is formed in an elongated cylindrical shape having the reference axis 300a as a central axis using hard resins, metals, or the like, and has an outer wall 322 that surrounds an outer periphery, and a lumen 324 that penetrates from a proximal end of the overtube body 320 to a distal end thereof.

The lumen 324 is provided with a space through which the endoscope insertion axis 306a and the treatment tool insertion axis 308a pass and which serves as the endoscope insertion passage 306 and the treatment tool insertion passage 308.

Additionally, the lumen 324 serves as an air supply pipe line through which a pneumoperitoneum gas sent thereinto from an air supply connector 318 passes.

The proximal end cap 340 is attached to a proximal end of the overtube body 320, and is formed in a columnar shape of which the diameter is made larger than the external diameter of the overtube body 320 using hard resins, metals, or the like. The proximal end cap 340 has a flat rear end surface serving as the proximal end surface 302 of the overtube 300 on a rear side thereof and has through-holes 342 and 344 that penetrate from the proximal end surface 302 to the lumen 324 of the overtube body 320.

The through-hole 342 has its central axis disposed coaxially with the endoscope insertion axis 306a, and forms a portion of the endoscope insertion passage 306. An opening of the through-hole 342 in the proximal end surface 302 is equivalent to the above-described endoscope insertion port 310.

The through-hole 344 has its central axis disposed coaxially with the treatment tool insertion axis 308a, and forms a portion of the treatment tool insertion passage 308. An opening of the through-hole 344 in the proximal end surface 302 is equivalent to the above-described treatment tool insertion port 314.

Valve members 346 and 348 are respectively disposed in the through-hole 342 and the through-hole 344. As the valve members 346 and 348, for example, there are provided slits that are open only in a case where the insertion part 102 and the treatment tool insertion part 202 are inserted therethrough and that are sealed up with outer peripheral surfaces of the insertion part 102 and the treatment tool insertion part 202 without a substantial gap. This secures the airtightness of spaces closer to the distal end side than the valve members 346 and 348, and reduces the leakage or the like of a pneumoperitoneum gas injected into the body cavity to the outside of the body.

The distal end cap 360 illustrated in FIG. 9 is attached to the distal end of the overtube body 320, and is formed of hard resins, metals, or the like. The distal end cap 360 has a front surface serving as the distal end surface 304 of the overtube 300 on a front side thereof and has through-holes 362 and 364 that penetrates from the lumen 324 of the overtube body 320 to the distal end surface 304.

The through-hole 362 has its central axis disposed coaxially with the endoscope insertion axis 306a, and forms a portion of the endoscope insertion passage 306. An opening of the through-hole 362 in the distal end surface 304 is equivalent to the above-described endoscope delivery port 312.

The through-hole 364 has its central axis disposed coaxially with the treatment tool insertion axis 308a, and forms a portion of the treatment tool insertion passage 308. An opening of the through-hole 364 in the distal end surface 304 is equivalent to the above-described treatment tool delivery port 316.

The slider 400 illustrated in FIG. 9 is accommodated within the lumen 324 of the overtube body 320, and is supported so as to be movable backward and forward in the direction of the reference axis 300a.

The slider 400 is coupled to the insertion part 102 inserted through the endoscope insertion passage 306 and the treatment tool insertion part 202 inserted through the treatment tool insertion passage 308, and moves one backward and forward in an interlocking manner with the backward and forward movement of the other in the forward-backward direction.

Additionally, the slider 400 is provided with a range of play where the insertion part 102 does not interlock with the backward and forward movement of the treatment tool insertion part 202 in the axial direction. That is, the insertion part 102 interlocks with the backward and forward movement of the treatment tool insertion part 202 in the axial direction with play.

Accordingly, if an operator performs the backward and forward movement operation of the treatment tool insertion part 202 in the axial direction, the insertion part 102 also moves backward and forward in an interlocking manner. Thus, the visual field, orientation, and the like of the endoscope 100 can be changed as intended by the operator. Hence, an assistant (endoscopic technician) who operates the endoscope 100 apart from the operator becomes unnecessary, and a troublesome condition in which the operator needs to instruct an assistant about the visual field, orientation, and the like of the endoscope 100 serially can be eliminated.

Additionally, in a case where the displacement of the treatment tool insertion part 202 in the axial direction is small, the insertion part 102 does not interlock. Therefore, the size of a target to be observed within an observation image can be prevented from fluctuating unnecessarily, a sense of perspective can be suitably maintained, and a stable observation image can be provided.

FIG. 10 is an enlarged cross-sectional view illustrating a portion, in which the slider 400 is disposed in FIG. 9, and illustrates a state where the insertion part 102 and the treatment tool insertion part 202 have been inserted through the endoscope insertion passage 306 and the treatment tool insertion passage 308, respectively.

As illustrated in FIG. 10, the slider 400 has a slider body 402. The slider body 402 is supported so as to be movable backward and forward in the forward-backward direction within the lumen 324, and is supported in a state where the movement of the slider body in the upward-downward direction and in the leftward-rightward direction and the rotation thereof in all directions is restricted.

Additionally, a range where the slider 400 moves backward and forward in the forward-backward direction with respect to the overtube body 320 becomes a range having a position where the slider 400 abuts against the proximal end cap 340 as a rear end, and having a position where the slider abuts against the distal end cap 360 as a front end.

An endoscope coupling part 420 is provided on the left side of the slider body 402, and secures a space serving as the endoscope insertion passage 306 within the lumen 324 of the overtube body 320. The slider 400 also moves backward and forward in an interlocking manner with the backward and forward movement of the insertion part 102 in the forward-backward direction.

In the overtube 300, the insertion part 102 and the treatment tool insertion part 202 are coupled together by the slider 400.

Next, an example of an operation method using the endoscopic surgical device 1 will be described.

FIGS. 11A to 15 are explanatory views illustrating states when the endoscopic surgical device 1 is operated.

Figure 11A:
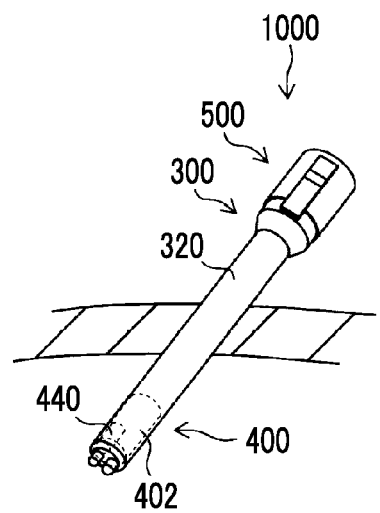
FIG. 11A is a view illustrating a state when the overtube is inserted into a body wall.
Figure 11B:
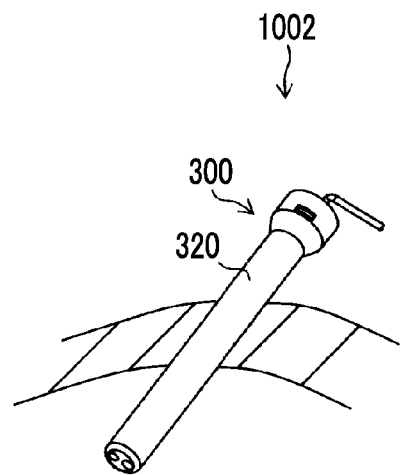
FIG. 11B is a view illustrating a state when the overtube is inserted into the body wall.
Figure 11C:
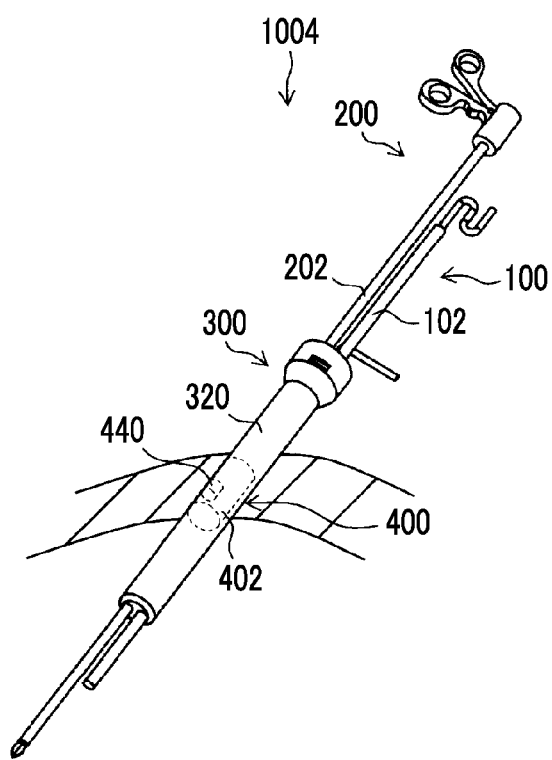
FIG. 11C is a view illustrating a state when the overtube is inserted into the body wall.

FIG. 11A to FIG. 11C are views illustrating states when the overtube 300 is inserted into a body wall.

FIGS. 12 and 13 are views illustrating states when the treatment tool insertion part 202 is pushed into an affected area side within a body cavity from the near side.

FIGS. 14 and 15 are views illustrating states when the treatment tool insertion part 202 is pulled from the affected area side within the body cavity to the near side.

First, as a preparation step for starting the operation of the endoscopic surgical device 1, the overtube 300 is inserted into a skin-incised area formed in a body wall in a state where the inner needle 500 is inserted through the endoscope insertion passage 306 and the treatment tool insertion passage 308 of the overtube 300, and the overtube 300 is inserted into a body cavity as in a state, indicated by reference sign 1000, of FIG. 11A.

Next, the inner needle 500 is extracted from the endoscope insertion passage 306 and the treatment tool insertion passage 308, as in a state, indicated by reference sign 1002, of FIG. 11B.

Next, the insertion part 102 is inserted into the endoscope insertion passage 306 from the endoscope insertion port 310 of the overtube 300, and the distal end of the insertion part 102 is delivered from the endoscope delivery port 312.

In this case, the insertion part 102 allows the endoscope coupling part 420 of the slider 400 to be inserted therethrough, and is coupled to the slider body 402 as described above. Accordingly, the insertion part 102 and the slider 400 are brought into an integrally moving state.

Subsequently, the treatment tool insertion part 202 is inserted into the treatment tool insertion passage 308 from the treatment tool insertion port 314 of the overtube 300, and the distal end of the treatment tool insertion part 202 is delivered from the treatment tool delivery port 316.

In this case, the treatment tool insertion part 202 allows a sleeve 440 of a treatment tool coupling part 422 of the slider 400 to be inserted therethrough, and is coupled to the sleeve 440 as described above. Accordingly, the treatment tool insertion part 202 and the sleeve 440 are brought into an integrally moving state.

If the preparation step is performed in this way, it will be in a state that can start operation of the endoscopic surgical device 1 as in a state, indicated by reference sign 1004, of FIG. 11C.

Next, a case where the treatment tool insertion part 202 is pushed into an affected area side within a body cavity from the near side will be described with reference to FIGS. 12 and 13.

First, in a case where the treatment tool insertion part 202 is minutely displaced in the axial direction as in a state, indicated by reference sign 1008, of the FIG. 12B from a state, indicated by reference sign 1006, of FIG. 12A, only the treatment tool insertion part 202 moves backward and forward, and the slider 400 does not move backward and forward. Hence, since the insertion part 102 does not move backward and forward, the range of an observation image displayed on the monitor 126 does not vary. For this reason, the size of an object to be observed can be prevented from fluctuating according to the minute displacement of the treatment tool insertion part 202, a sense of perspective can be suitably maintained, and a stable observation image can be obtained.

In contrast, in a case where the treatment tool insertion part 202 is greatly displaced in the axial direction like from a state, indicated by reference sign 1006, of FIG. 13A, which is the same state as reference sign 1006 of FIG. 12A, to in a state, indicated by reference sign 1010, of FIG. 13B, the slider 400 moves backward and forward in an interlocking manner with the backward and forward movement of the treatment tool insertion part 202. In this case, since the insertion part 102 moves backward and forward, the range of an observation image displayed on the monitor 126 is continuously changed so as to follow the backward and forward movement of the treatment tool insertion part 202. Accordingly, since the size of a target to be observed varies according to the operation of the treatment tool 200, it is possible for an operator to simply obtain a desired image.

Additionally, the same is true in a case where the treatment tool insertion part 202 is pulled from an affected area side within a body cavity to the near side.

Figure 14A:
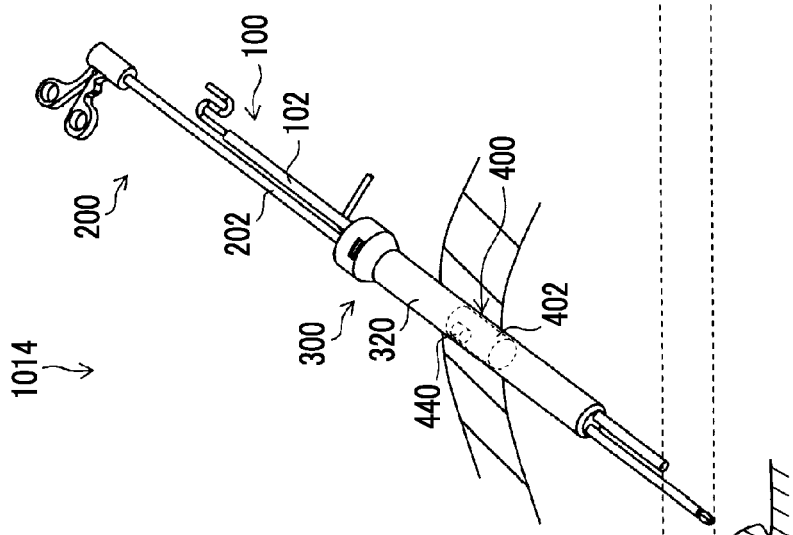
FIGS. 14A and 14B are views illustrating a state when the treatment tool insertion part is pulled from the affected area side within a body cavity to the near side.
Figure 14B:
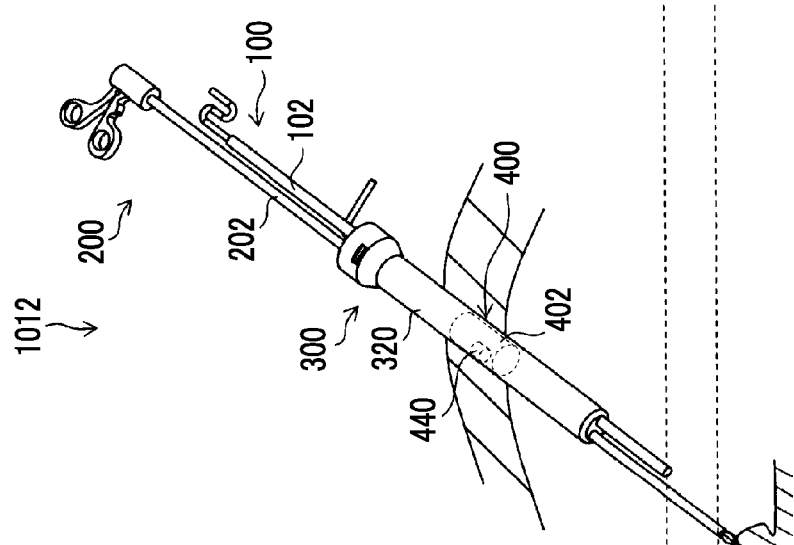

That is, in a case where the treatment tool insertion part 202 is minutely displaced in the axial direction like from a state, indicated by reference sign 1012, of FIG. 14A to a state, indicated by reference sign 1014, of FIG. 14B, only the treatment tool insertion part 202 moves backward and forward, and the slider 400 does not move backward and forward. Hence, since the insertion part 102 does not move backward and forward, the range of an observation image displayed on the monitor 126 does not vary. For this reason, the size of an object to be observed can be prevented from fluctuating according to the minute displacement of the treatment tool insertion part 202, a sense of perspective can be suitably maintained, and a stable observation image can be obtained.

In contrast, in a case where the treatment tool insertion part 202 is greatly displaced in the axial direction like from a state, indicated by reference sign 1012, of FIG. 15A, which is the same state as reference sign 1012 of FIG. 14A, to a state, indicated by reference sign 1016, of FIG. 15B, the slider 400 moves backward and forward in an interlocking manner with the backward and forward movement of the treatment tool insertion part 202. In this case, since the insertion part 102 moves backward and forward, the range of an observation image displayed on the monitor 126 is continuously changed so as to follow the backward and forward movement of the treatment tool insertion part 202. Accordingly, since the size of a target to be observed varies according to the operation of the treatment tool 200, it is possible for an operator to simply obtain a desired image.

EXPLANATION OF REFERENCES

1: endoscopic surgical device
10: optical unit
100: endoscope
102: insertion part
104: operating part
106: optical member
108: cover glass
110: optical lens
112: prism
114: imaging device
116: signal line
122: signal line
124: processor device
126: monitor
128: optical fiber element wire
130: light source device
131: outer tube
132: holding tube
134: cover glass fixing part
136: cover glass position restricting part
138: optical lens position restricting part
140: lens barrel
142: distal end flange part
144: spacer
146: window part
148: antireflection treatment layer
150: gap
152: through-hole
154: inner peripheral surface
156: region
158: first inner wall surface
160: first bottom surface
162: first recess
164: second inner wall surface
166: second bottom surface
168: second recess
170: optical unit
172: holding tube
174: third inner wall surface
176: third bottom surface
178: spacer
180: third recess
200: treatment tool
202: treatment tool insertion part
204: operating part
206: treatment part
300: overtube
302: proximal end surface
304: distal end surface
306: endoscope insertion passage
308: treatment tool insertion passage
310: endoscope insertion port
312: endoscope delivery port
314: treatment tool insertion port
316: treatment tool delivery port
318: air supply connector
320: overtube body
322: outer wall
324: lumen
340: proximal end cap
342, 344: through-hole
346, 348: valve member
360: distal end cap
362, 364: through-hole
400: slider
402: slider body
420: endoscope coupling part
422: treatment tool coupling part
440: sleeve

What is claimed is:

1. An optical unit having a distal end, a proximal end, and an optical axis in a first axial direction, the optical unit comprising:
a cover glass having an incidence surface on the distal end side, an emission surface on the proximal end side, and a side surface;
an optical lens disposed on the emission surface side of the cover glass;
a holding tube having a cover glass fixing part that fixes the side surface of the cover glass, a cover glass position restricting part that restricts a position of the cover glass in the first axial direction, and an optical lens position restricting part that restricts a position of the optical lens in the first axial direction; and
a spacer that is disposed between the cover glass and the cover glass position restricting part, has a first end surface and a second end surface at both ends thereof in the first axial direction, and has a window part serving as an optical channel in the first axial direction between the first end surface and the second end surface, the first end surface being a surface disposed on the cover glass side, an external diameter of the first end surface being smaller than an internal diameter of the cover glass fixing part,
wherein the holding tube includes a cover glass accommodating part that includes an inner wall and a bottom surface, and accommodates the cover glass and the spacer, wherein the inner wall of the cover glass accommodating part includes the cover glass fixing part that faces the side surface of the cover glass, wherein the bottom surface of the cover glass accommodating part includes the cover glass position restricting part that faces the second end surface of the spacer and fixes the spacer, wherein, when a direction perpendicular to the first axial direction is defined as a second axial direction and a direction perpendicular to the first axial direction and the second axial direction is defined as a third axial direction, the cover glass position restricting part restricts positions of the spacer in the first axis direction, the second axis direction and the third axis direction, and wherein a solder pool is provided in a region surrounded by the cover glass accommodating part, the cover glass and the spacer.

2. The optical unit according to claim 1,
wherein the cover glass accommodating part includes
a first recess that has a first inner wall surface and a first bottom surface, and accommodates the cover glass, and
a second recess, that has a second inner wall surface and a second bottom surface, is open to the first bottom surface of the first recess, and accommodates the spacer,
wherein the first inner wall surface is provided at a position that faces the side surface of the cover glass and has the cover glass fixing part,
wherein the second bottom surface is provided at a position that faces the second end surface of the spacer and has the cover glass position restricting part,
wherein an internal diameter of the second inner wall surface is made smaller than an internal diameter of the first inner wall surface, and a depth of the second recess in the first axial direction is made smaller than a thickness of the spacer in the first axial direction, and
wherein the solder pool part is disposed in a region surrounded by the first recess, the cover glass, and the spacer.

3. The optical unit according to claim 1,
wherein the cover glass accommodating part has a third inner wall surface and a third bottom surface and has a third recess that accommodates the cover glass and the spacer,
wherein the third inner wall surface is provided at a position that faces the side surface of the cover glass, and has the cover glass fixing part,
wherein the third bottom surface is provided at a position that faces the second end surface of the spacer, and has the cover glass position restricting part, and
wherein the spacer has a stepped part configured such that the external diameter of the first end surface is smaller than an external diameter of the second end surface, and the solder pool part is disposed between the third inner wall surface and the stepped part.

4. The optical unit according to claim 1,
wherein a metallized layer is formed on the side surface of the cover glass, and a plated layer is formed on the cover glass fixing part.

5. The optical unit according to claim 1,
wherein the spacer has an antireflection treatment layer on at least the first end surface, and
wherein a reflectivity of the antireflection treatment layer of the spacer is 10% or less.

6. The optical unit according to claim 1,
wherein the window part has a through-hole that allows a first opening part formed on the first end surface and the second opening part formed on the second end surface to communicate with each other, and
wherein an opening diameter of the first opening part is made smaller than an opening diameter of the second opening part, and the through-hole has a tapered inner peripheral surface of which an internal diameter becomes gradually smaller from the second end surface toward the first opening part side.

7. The optical unit according to claim 1,
wherein the cover glass fixing part restricts positions of the cover glass in the second axial direction and the third axial direction.

8. An endoscope comprising:
an insertion part inserted into the body; and
an optical unit that is provided at a distal end part of the insertion part and has a distal end, a proximal end, and an optical axis in a first axial direction,
wherein the optical unit includes
a cover glass having an incidence surface on the distal end side, an emission surface on the proximal end side, and a side surface,
an optical lens disposed on the emission surface side of the cover glass,
a holding tube having a cover glass fixing part that fixes the side surface of the cover glass, a cover glass position restricting part that restricts a position of the cover glass in the first axial direction, and an optical lens position restricting part that restricts a position of the optical lens in the first axial direction, and
a spacer that is disposed between the cover glass and the cover glass position restricting part, has a first end surface and a second end surface at both ends thereof in the first axial direction, and has a window part serving as an optical channel in the first axial direction between the first end surface and the second end surface, the first end surface being a surface disposed on the cover glass side, an external diameter of the first end surface being smaller than an internal diameter of the cover glass fixing part, and an antireflection treatment layer being provided on at least the first end surface,
wherein the holding tube includes a cover glass accommodating part that includes an inner wall and a bottom surface, and accommodates the cover glass and the spacer,
wherein the inner wall of the cover glass accommodating part includes the cover glass fixing part that faces the side surface of the cover glass,
wherein the bottom surface of the cover glass accommodating part includes the cover glass position restricting part that faces the second end surface of the spacer and fixes the spacer,
wherein, when a direction perpendicular to the first axial direction is defined as a second axial direction and a direction perpendicular to the first axial direction and the second axial direction is defined as a third axial direction, the cover glass position restricting part restricts positions of the spacer in the first axis direction, the second axis direction and the third axis direction, and
wherein a solder pool is provided in a region surrounded by the cover glass accommodating part, the cover glass and the spacer.

* * * * *